(12) United States Patent
Vilkomerson et al.

(10) Patent No.: US 8,052,608 B2
(45) Date of Patent: Nov. 8, 2011

(54) TRANSDUCER APPARATUS AND METHOD FOR INTRAVASCULAR BLOOD FLOW MEASUREMENT

(75) Inventors: David Vilkomerson, Princeton, NJ (US); Thomas A. Chilipka, East Windsor, NJ (US); John W. Bogan, Nazareth, PA (US)

(73) Assignee: DVX, LLC, Princeton, NJ (US)

( * ) Notice: Subject to any disclaimer, the term of this patent is extended or adjusted under 35 U.S.C. 154(b) by 1022 days.

(21) Appl. No.: 11/986,164

(22) Filed: Nov. 20, 2007

(65) Prior Publication Data
US 2008/0139940 A1   Jun. 12, 2008

Related U.S. Application Data

(60) Provisional application No. 60/861,852, filed on Nov. 30, 2006.

(51) Int. Cl.
*A61B 8/00* (2006.01)

(52) U.S. Cl. ........ 600/462; 600/407; 600/437; 600/459; 600/454; 600/438

(58) Field of Classification Search .................. 600/407, 600/309, 504, 438, 454, 459, 437, 462
See application file for complete search history.

(56) References Cited

U.S. PATENT DOCUMENTS

| | | | | |
|---|---|---|---|---|
| 5,488,953 A | * | 2/1996 | Vilkomerson | 600/454 |
| 5,807,258 A | * | 9/1998 | Cimochowski et al. | 600/454 |
| 2005/0070799 A1 | | 3/2005 | Vilkomerson et al. | |

OTHER PUBLICATIONS

Evans et al, Doppler Ultrasound, John Wiley & Sons, (2000).

* cited by examiner

*Primary Examiner* — Brian Casler
*Assistant Examiner* — Joel Lamprecht
(74) *Attorney, Agent, or Firm* — Keene IP Law (57) ABSTRACT

Transducers to measure fluid flow using Doppler ultrasound that are suitable for integrating into or connecting to intravascular devices are disclosed. These transducers meet the requirement for long, thin, flexible transducers, and consist of one or more diffraction-grating transducers, with or without non-diffraction-grating transducers. An exemplary configuration of the transducers utilizes the diffraction caused by narrow transducers to produce beam overlap for Doppler detection of moving blood, and stripline transmission lines are used to bring energy to and receive energy from the transducers and may carry the disclosed transducer configurations as well as carry signals into and out of the blood vessels.

17 Claims, 12 Drawing Sheets

Variation of $Z_0$ for Different Dielectric Constants and Aspect Ratio

TRANSDUCER APPARATUS AND METHOD FOR INTRAVASCULAR BLOOD FLOW MEASUREMENT

RELATED APPLICATION

This application claims priority of U.S. Provisional Patent Application Ser. No. 60/861,852, entitled TRANSDUCER MEANS FOR INTRAVASCULAR BLOOD FLOW MEASUREMENT, filed Nov. 30, 2006, the entire disclosure of which is hereby incorporated by reference as if being set forth in its entirety herein, and relates to co-pending U.S. patent application Ser. No. 10/953,276 entitled VESSEL FLOW MONITORING SYSTEM AND METHOD, filed Sep. 29, 2004, which application claims priority to Provisional Patent Application Ser. No. 60/507,070 filed Sep. 29, 2003, the entire disclosures of which are incorporated by reference as if being set forth in their entireties herein.

FIELD OF THE INVENTION

This invention provides transducer apparatus and methods for measuring blood flow within blood vessels. These transducers may be incorporated into stents and other such implantable permanent or temporary intravascular devices.

BACKGROUND OF THE INVENTION

Blood flow keeps tissue alive. Measuring that flow is an important medical need. Doppler ultrasound methods utilize the change in frequency of ultrasound backscattered from moving blood to deduce the velocity of the scatterers; such Doppler methods are well-known, and used extensively clinically. (See a text entitled, *Doppler Ultrasound*, by David H Evans and W. Norman McDicken, John Wiley & Sons, Chichester, 2000.)

U.S. published patent application Ser. No. 10/953,276 filed on Sep. 29, 2004 (referred to here as the '276 application, and incorporated herein by reference in its entirety), assigned to the assignee herein, taught means and methods of measuring blood flow within vessels with ultrasound transducers mounted in or upon the vessel wall. These means and methods used the Doppler effect and certain ultrasound transducers, known as diffraction-grating transducers ("DGT"), alone or in association with conventional, non-DGT transducers.

It would be desirable, however, to be able to measure flow in blood vessels without the need to embed the transducers in an artificial graft or place them on the outer wall of a vessel— without the need for surgical incision. Over the last several decades, catheter procedures have been developed to permanently place metallic structures (such as stents to prop open arteries), or temporarily place such structures (such as vena cava filters to stop post-operative blood clots from going to the lung), and now are part of usual medical care, known as minimally invasive procedures.

There are many clinical situations where a physician desires to place a flow sensor by these minimally invasive means, whether permanently to measure blood flow, e.g. in the coronary arteries of the heart, or temporarily, e.g. post-operatively to evaluate the success of a transplant or other major surgical event. Stents and vena cava filters must be small in diameter so they can enter the blood vessel within a catheter, and be flexible to expand to fit against the blood vessel's walls. Rigid, rectangular piezoceramics transducers, as described in the '276 application, cannot easily be incorporated into the required thin, flexible, expandable mesh-like structures needed for minimally invasive stents and vena cava filters.

SUMMARY OF THE INVENTION

In order to make feasible implantable intravascular flow sensors, we disclose means and methods for using long, narrow, thin flexible transducer elements, able to be incorporated into catheter-placed expandable structures or into structures connected to them, for Doppler ultrasound measurement of intravascular blood flow. Apparatus for measuring flow comprising: a first elongated narrow ribbon like transducer of a given length comprising alternating sections of piezoelectric and separation media, means for applying a signal to the transducer to cause the transducer to transmit a beam along a predetermined path relatively parallel with the length of the transducer while the diffraction operative from the narrow ribbon spreads the beam therefrom in the direction perpendicular to the length of the transducer.

BRIEF DESCRIPTION OF THE FIGURES

FIG. 1 (b) is a prior art structure for continuous-wave ("CW") Doppler.

FIG. 2 (a) is a schematic representation of the cross-section of a flexible double-beam DGT consisting of alternating polarized piezoceramic segments separated by polymer; FIG. 2 (b) shows the construction of a flexible non-DGT transducer (non-alternating polarization).

DETAILED DESCRIPTION OF THE INVENTION

Figure 2A:
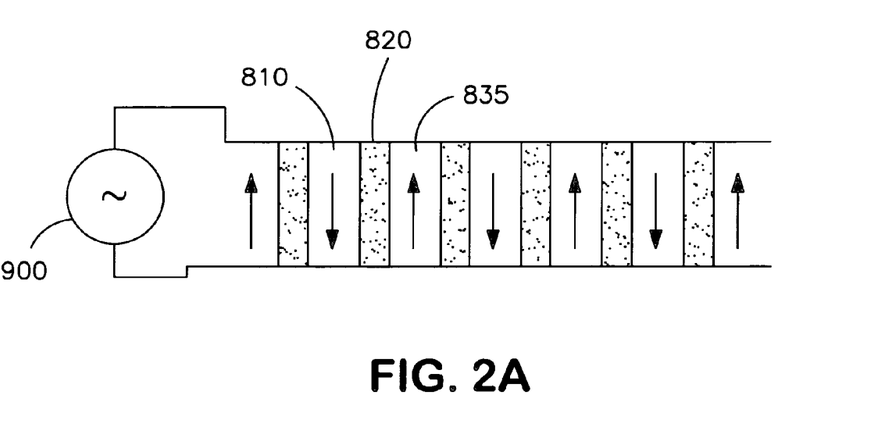

A double-beam DGT (as taught in the '276 application) comprises alternately polarized piezoelectric elements 810 separated by inactive material, as shown in FIG. 2 (A); if the separating elements 820 between the piezoelectric elements are made of flexible polymer, the DGT, when mounted on a flexible metal strut, will be flexible. The DGT of FIG. 2 is driven and energized by a source 900.

Figure 2B:
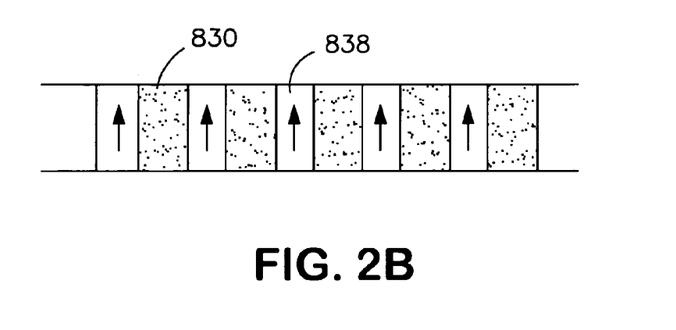

Referring to FIG. 2B, if the piezoelectric elements 838 are not alternately polarized, but just separated by flexible polymer 830, a non-DGT flexible transducer element is made. (Separating piezoceramics is known to actually improve transducer performance; those familiar with the art know them as "2-2 composites".)

However, there is a practical limitation to employing the configurations as shown in the '276 application (see FIG. 1b) if the transducers are fabricated on narrow elements: the transducers' active areas are limited, leading to high electrical impedance transducers (as the impedance is inversely related to the area) that are difficult to transfer electrical energy to and from (i.e., "poorly matched").

Figure 3:
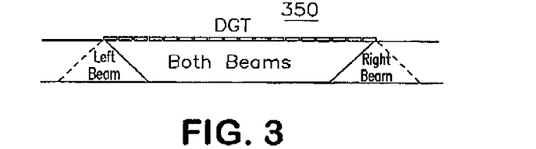
FIG. 3 shows, in longitudinal view of a vessel, the sensitive volume (beam overlap) produced by a pulsed-wave DGT useful for pulsed-wave Doppler.

For the pulsed-wave Doppler taught in FIG. 1 of the '276 application (reproduced as FIG. 1 herein)—which consists of a single DGT 10 excited by a short pulse that then receives backscattered ultrasound with Doppler-shifted frequency from which the blood velocity can be deduced—the problem can be circumvented by extending the DGT for the length of the device, e.g. 20 mm. As shown in FIG. 3, the sensitive volume, where the beams overlap, extends the length of the DGT device 350.

There are two major drawbacks to this configuration of FIG. 3; half of the Doppler energy (that produced by the left-going transmit beam and the right-going receive beam) is received as a zero-frequency Doppler shift. This is taught in the '276 application as the Doppler shift which is the sum of the Doppler effect of the scattering blood cells from the transmitted beam and from the receiving beam. Therefore, as the angle of the beam going left is the opposite of the beam going right, the sum of the Doppler shifts from the beams produces zero net Doppler shift. The other half of the backscattered signal, from the left-going beam receiving energy from the left-going transmit beam, and similarly for the right-going beam, does create a valid Doppler signal. The other drawback to this Doppler configuration is that it requires pulsed-wave operation, meaning the DGT 350 must be made to have short acoustic ringdown (e.g., for a 3 mm vessel, less than 2 microseconds). The maximum velocity Doppler signals occur about 2 microseconds after the transducer is pulsed, which requires matching layers and backing layers not easily made on thin narrow structures. The driving electronics must have high speed transmit/receive switches, which significantly complicates the electronic requirements and increases the power demand, both undesirable factors for implanted electronics. As short ringdown DOT's continue to have practical limitation's, and as simple, low-power electronics are more desirable for implantable devices, we will consider configurations suitable for CW Doppler in the remaining parts of this disclosure.

Figure 1A:
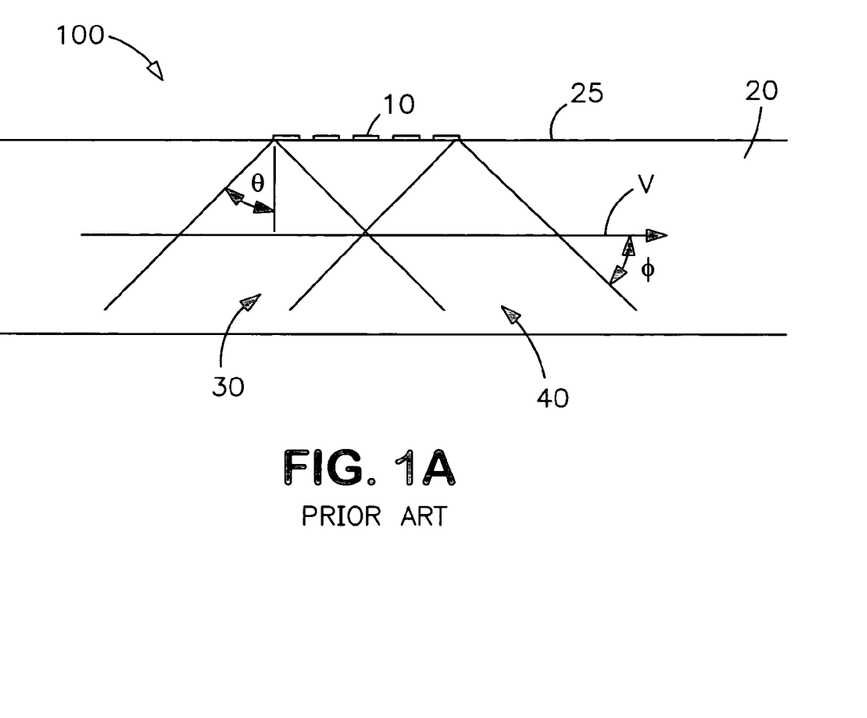
FIG. 1a shows, a DGT used for pulse-mode Doppler measurement according to the prior art.
Figure 1B:
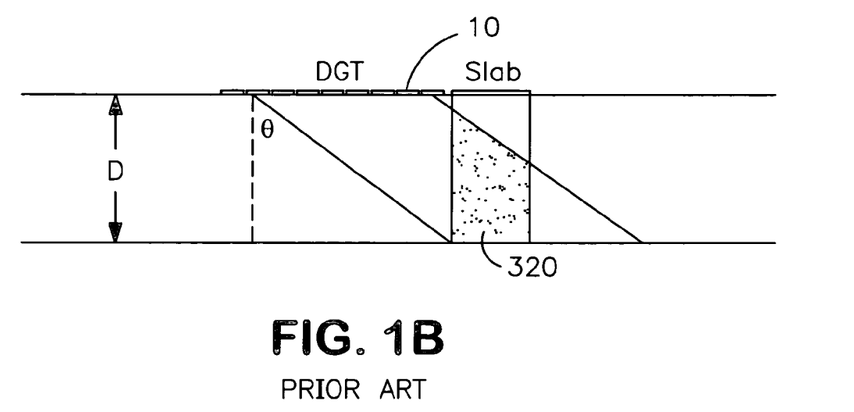

Extending the DGT in the CW (Continuous Wave) configuration of FIG. 1(B) by trying to increase the transducer area is not a viable solution. The sensitive area, i.e. the region where the beams overlap, such as the volume marked 320 in FIG. 1(B), does not increase once the length of the DGT, 10, exceeds $\tan \theta * D$, with $\theta$ and D as shown in FIG. 1B. Energy launched by the DGT that does not overlap the receiving beam is wasted, as it will not be received (not being in the beam) of the non-DGT "slab" transducer. If, for example, the diameter D is 3 millimeters, as would be a coronary artery, and $\tan \theta \sim 1$ (if 0 is made larger, the transducer is not as efficient), the length is limited to approximately 3 millimeters. If the width of the active area of the transducer is 100 micrometers (μm), as typical for a thin, flexible element, the area would be only 0.3 mm$^2$; at 20 MHz, this would correspond to 350 ohms impedance resulting in a severe mismatch to the usual 50-ohm impedance signal cable. (Space limitations typically preclude placing impedance matching circuits inside a device implantable in the body.)

One way of solving this problem is to repeat the sequence shown in FIG. 1(A), i.e. repeating the transducer arrangement of DGT 810—non-DGT 820, DGT 835, etc., multiple times along the length of the transducer element. However, a thin supporting metal element required to keep the device flexible will not effectively decouple the transmitting transducer from the receiving transducer, i.e. there will be high "cross-talk" that, at the least, will reduce the sensitivity of the system. Further, it is difficult to fabricate the interconnections between the various transmitter sections and receiver sections (to be electrically in parallel to reduce the impedance) within the narrow confines of these elements.

Referring back to the 3 mm length transducer of FIG. 1B, note that if the active length could be made about 20 millimeters long, which is the typical length of a stent or vena cava filter, the transducer area would increase by a factor proportional to the length, (i.e., 20/3 as much), and therefore its impedance would decrease to (3/20) of the 3 mm transducer's 350 ohms, or about 58 ohms impedance. This represents a good match to the usual 50 ohm signal line impedance (and which may be matched more closely using further impedance matching procedures).

Figure 4:
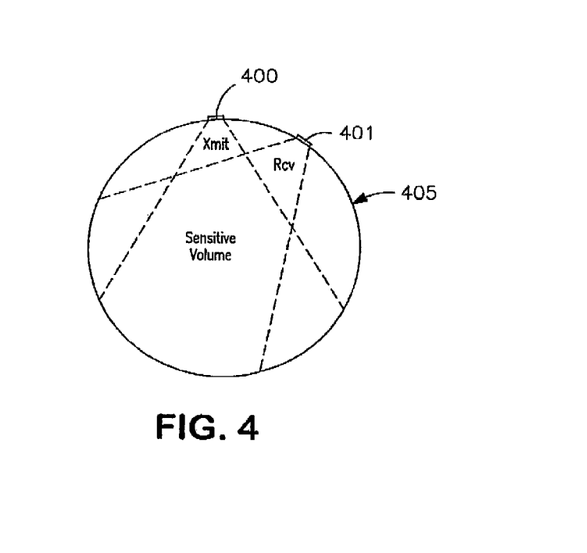
FIG. 4 shows, in cross-section view of a vessel, the sensitive volume produced from a narrow DGT and narrow non-DGT transducer useful for CW Doppler operation.

Of course the area can be increased by making the elements wider. Such wide elements are less usable in stent and other intravascular devices. Moreover, as shown explicitly in Eq. 3, below, the spreading of the beam in the direction perpendicular to the length of the transducer becomes narrower and narrower as the width increases. For an element many wavelengths across, e.g. for 20 MHz a transducer 0.75 mm wide (10λ), the beam "cone" of FIG. 4 will be (from Eq. 5) only 50 from the perpendicular. It the two beams of FIG. 4 are from such transducers, they would cross each other only at a narrow intersection, which may not be at the highest velocity point in the vessel and therefore give incorrect results. We will consider, then, only narrow, i.e. <3λ, elements from which diffraction produces good beam spreading; this produces a large "sensitive volume", as it is known in the art, where the beams cross and therefore blood flow can be measured.

We disclose means for providing for flexible extended-length transducers with excellent sensitive volume (beam overlap). This is achieved by using diffraction perpendicular to the long axis of a DGT and similarly-lengthed non-DGT. Then one can form a sensitive volume, i.e. where the send and receive beams overlap, as shown in FIGS. 3 & 4. This sensitive volume, where any moving blood will produce a Doppler-shifted frequency, can occupy most of the length of the device. As the two transducers are on separate elements, cross-talk is virtually eliminated, and there is no zero-frequency Doppler term (as there was with the single DGT) and connections can be easily made at one end of each element. In this way, the requirement for sufficient transducer area needed for efficient operation but using thin flexible narrow transducers as needed for intravascular catheter-placed flow measuring devices can be satisfied. As seen in FIG. 4 a vessel 405 such as an artery has positioned about the periphery a transmit (XMIT) DGT 400 and spaced apart is a receive (RCV) DGT 401.

Exemplary embodiments associated with the design adaptation and configuration of these transducers, including how long, how narrow, and how to configure such transducers is provided.

For example, a 150 micron (μm) wide, 2 centimeter (cm) long element of an implantable device can be coated with a 100 micron-thick lead-free biocompatible piezoceramic (e.g., KNN-LT-LS (described by Safari and Hagh, Proceedings of 2006 IEEE Ultrasonics Symposium)) for operation at a resonant frequency of 20 megahertz (MHz). At this frequency, a stainless steel element 316 (often used in such devices because of its biocompatibility) of half-wavelength thick (ensuring it provides a mismatch to the rear face of the piezoceramics for effective transducer operation) is 145 microns (calculated by 0.5*λ=0.5*acoustic velocity in 316 steel/frequency), a useful thickness for flexible device components.

The impedance of the transducer is found from the characteristics of the piezoceramics and the area of the transducer. This piezoceramics has a relative permittivity of 600 so that the electrical impedance Z is $$Z = (2 \times \pi \times f \times C)^{-1} \quad (1)$$

where C is found from the characteristics of the piezoceramic as $$C = k \times \varepsilon_0 \times A \times d^{-1} \quad (1a)$$
$$= k \times \varepsilon_0 \times A \times \frac{f}{Fc}$$

where Fc is the frequency constant of the piezoceramics material, derived from the velocity in the material and the resonance condition for the film. With k=600, the area assumed to be 150 micron wide by 2 cm long, and the thickness d of 100 microns, the value of Z using eq. 1 is 50 ohms, a perfect match to the usual impedance of a signal cable.

To determine the dimensions of the elements for the DGT transducer shown in FIG. 2A+2B, one solves:

$$\sin \theta = \lambda / \text{spatial period}, \quad (2)$$

where the period is given by the spacing between elements 810 and 820 with the same polarization distance; for θ=300, therefore, period=2λ.

As $$\lambda = f / \text{velocity of sound}$$

in blood where the velocity of sound is $1.5 \cdot 10^3$ meters/sec and f is 20 MHz, $$\lambda = 75 \text{ microns}$$

and therefore the spatial period 2λ is 150 microns. This means the center-to-center distance between the alternately polarized elements in FIG. 2 is 75 microns.

Figure 5:
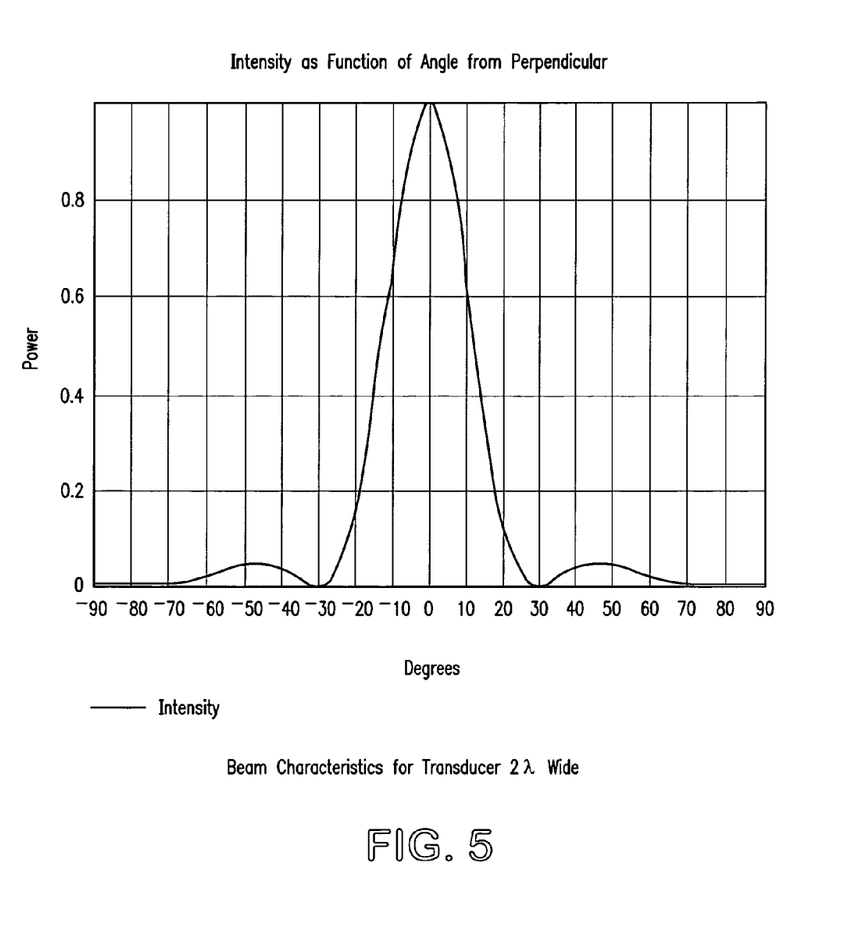
FIG. 5 shows the distribution of energy from a narrow (2λ wide) transducer in the direction perpendicular to the long axis of the narrow transducer. It should be noted that if the width a is much greater than the wavelength, the beam projects without spreading, i.e. like a laser beam.

The diffraction pattern of the beam, spreading outward perpendicularly from the long axis of the transducer, is given by the calculations for a narrow aperture: (Born and Wolf, Principles of Optics, $3^{rd}$ Ed., pg 363)

$$P(\theta, a) = \left[ \frac{\sin\left(\frac{2\pi}{\lambda} \sin\theta * a\right)}{\frac{2\pi}{\lambda} \sin\theta * a} \right]^2 \quad (3)$$

where P is the power, a=the half-width of the transducer, λ the acoustic wavelength, and θ the angle from the perpendicular to the transducer face. The distribution of power versus angle for a 2% transducer is shown in FIG. 5.

With a transducer 150 microns wide, i.e. a=λ, the angular width of the lobe of power is contained within the angle θ found for sin θ=½, i.e. θ=30 degrees. (In equation 3, the argument of the outer sin function reduces to π when sin θ=½, making P at that angle θ=30 degrees equal to zero.) The beams depicted in FIG. 4 show the energy spreading out in such a 30-degree conical pattern.

In the example shown in FIG. 4 placing these elements 400 (XMIT) and 401 (RCV) as shown, approximately 35 degree angular separation, produces a desirable sensitive volume, in that it covers the center of the vessel 405, for this 3 mm diameter vessel 405. With the design parameters of width and/or frequency, which parameters may be set by the device requirements and the characteristics of the piezoceramic used, and a particular vessel diameter, a different angular separation between the two transmit transducer 400 and receive transducer 401 may be desirable. (For example, for a large diameter vessel, relatively narrow diffraction cones will still intersect at the center of the vessel where the velocity is highest.

The equations above show how to determine the impedance as a function of frequency and area and how the diffraction pattern will vary with the frequency and transducer width. With these quantities and the knowledge of the vessel diameter the appropriate configuration for measuring the flow can be determined.

It should also be noted that more than one receiver can be used with a transmitter, or multiple transmitters used with one or more receivers, as insonated blood scatters in all directions. Again, once the diffraction patterns are calculated as taught above, various configurations of transmitting and receiving transducers can be arranged. If these transducers are connected in parallel, the overall impedance will be reduced by a factor equal to the number in parallel; if connected in series, the impedance will rise proportionally to the number connected in series, etc. The number of transducer elements is constrained by mechanical considerations of the device and size of vessel in which it is to be placed.

The CW configuration described and shown in FIG. 4 is practical for implantable devices because it does not require a transmit-receive switch, i.e. the DGT as 400 is always transmitting (or receiving) and the non-DGT transducer is always receiving as 401 (or transmitting, if the DGT is receiving—either way works).

Figure 6:
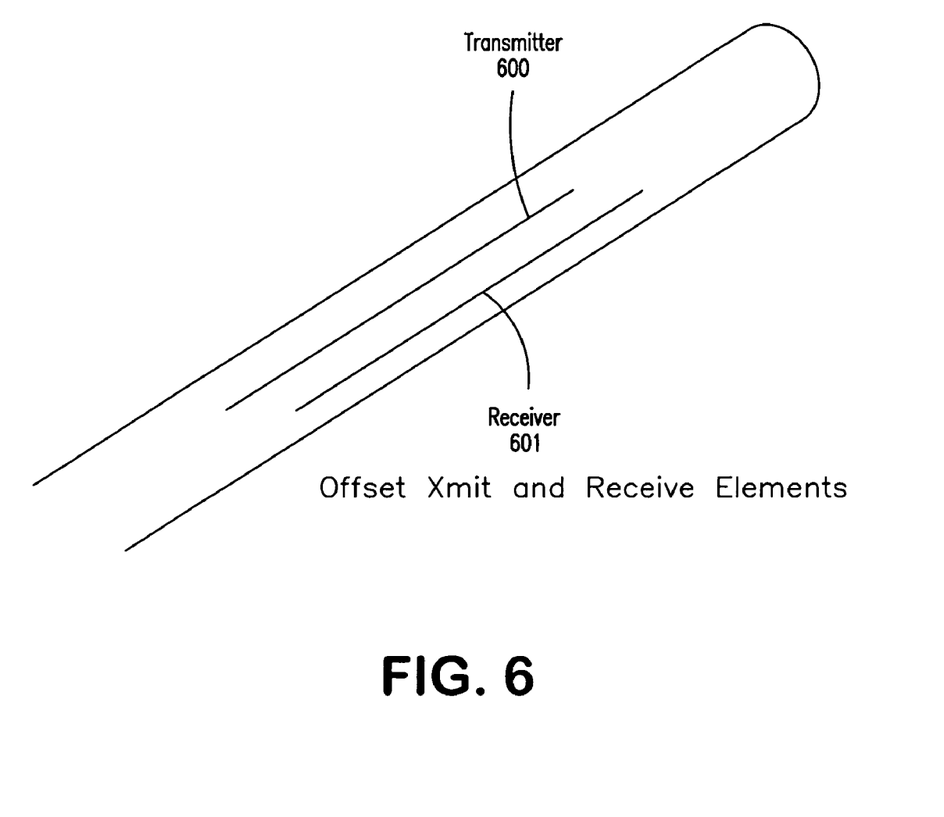
FIG. 6 is a configuration that provides for directional Doppler information by affecting a longitudinal offset between two transducer elements.

Referring to FIG. 3, DGT 350 produces two symmetrical, equal-power beams (left and right), the moving blood will produce two equally Doppler-shifted frequencies of equal power; i.e. mirror image frequency components above and below zero frequency, so no direction information can be obtained. Referring to FIG. 6, direction information can be regained by offsetting the DGT 600 in relation to the non-DGT transducer 601. Because there is greater overlap between the transmitted and receiving beams in one direction, Doppler signals from blood moving to the right, and therefore generating a negative Doppler shift, will be stronger than the positive Doppler shift generated from the left-going beam from the transmitter. Therefore, a stronger negative Doppler shift means (for this example) right-moving blood, and stronger positive Doppler shift, left-moving blood. Referring to FIG. 5 which shows power versus angle, one can see there is a greater overlap between the transmitted and received beams in one direction. Therefore, from measuring which Doppler signal has more power, the direction of the flow can be determined, e.g. in the case of FIG. 5 to the right.

Figure 7:
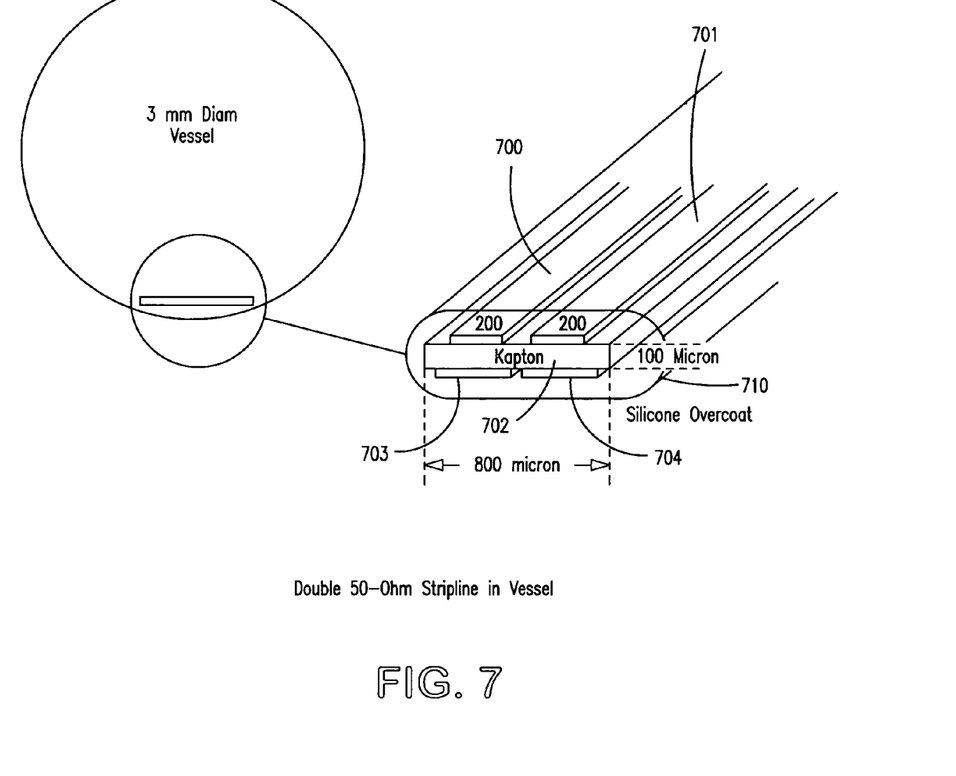
FIG. 7 is a schematic representation, inside a vessel, of a stripline cable to connect the two transducers of FIG. 6 to the interface for communicating externally from the body.

In an exemplary configuration, these two elements can be placed around the periphery of a device and the DGT will insonate the moving blood in the vessel and the non-DGT transducer will detect the Doppler-shifted signal. The DGT can be driven by one part of an impedance-matched double-stripline, shown in FIG. 7, and the receiving non-DGT transducer by the other. Striplines can be thin flexible structures consisting of a narrow strip of conductor separated from a conducting ground plane by a dielectric, which can be a flexible polymer like Kapton (Kapton is a registered trademark of DuPont), as shown in FIG. 7 for our exemplary device. (Striplines are well-known to those skilled-in-the-art.). As the power levels in implantable devices is very low, typically milliwatts, the low current used can be carried by very thin metal stripes, and small stripline structures are feasible, allowing them to lie on the wall of the blood vessel without affecting blood flow. In FIG. 7 the stripline has a central dielectric core 702 on a top surface these are positioned parallel conductors 700 and 701 with corresponding parallel conductors 703 and 704 on the bottom surface. The conductors 703 and 704 operate as the ground terminals.

Figure 8:
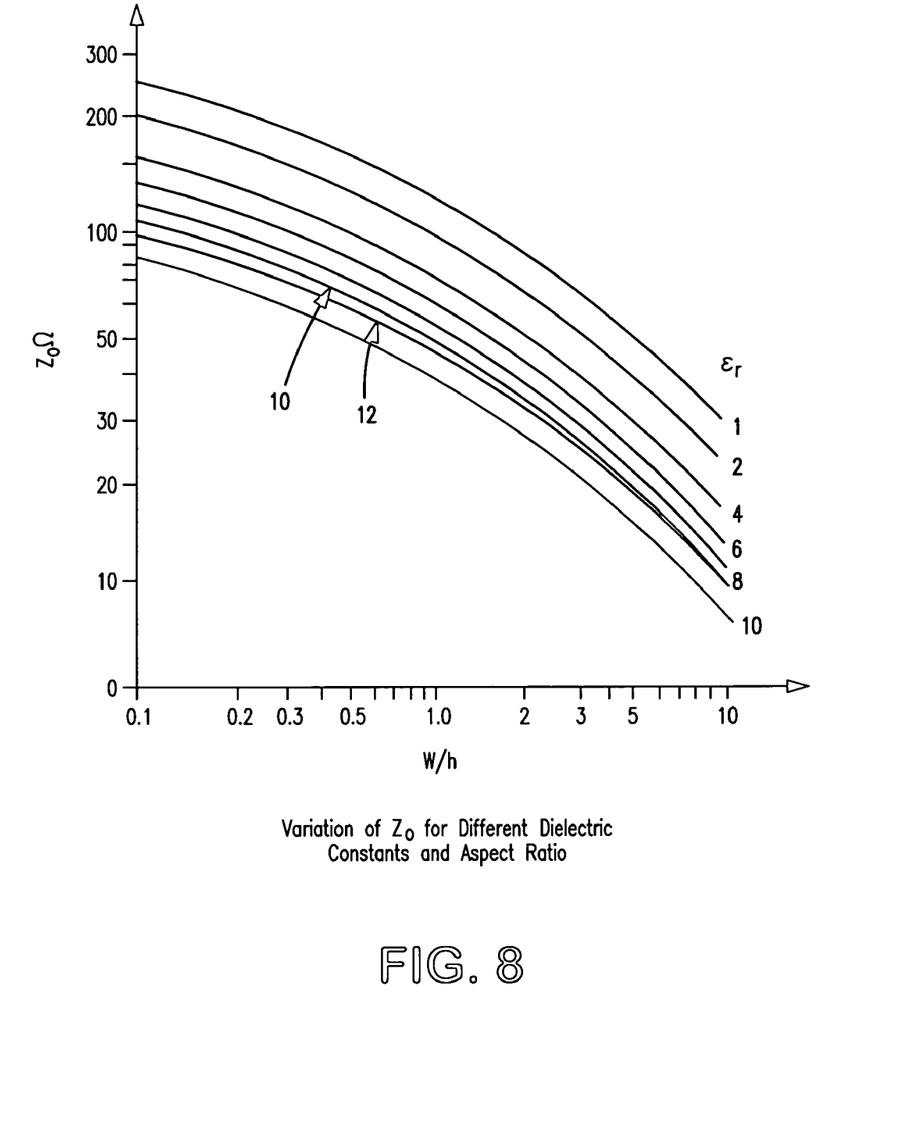
FIG. 8 displays a graph from the Electronics Designer's Handbook, L. Giacolieto, Ed., McGraw-Hill, New York, 1977; pg 8-54, of the impedance of the stripline of FIG. 7 as a function of width-to-height and relative dielectric coefficient of the material that can be used to adjust a stripline impedance to match the transducers.

The stripline can be "tuned" to match the transducer impedance as indicated in FIG. 8 (Electronics Designer's Handbook, L. Giacolleto, Ed., McGraw-Hill, New York, 1977; pg 8-54), which shows how the impedance of a stripline such as shown in FIG. 7 varies with the width-to-thickness of the stripline and the dielectric constant. For the 50 ohm transducers described, a 200 micron-wide conductor (700, 701, 703, 704) on a 4-mil (100 micron) Kapton dielectric ($\in=4$) 702, with a ground plane produces a 50 coax-like signal cable for the transmitter and receiver. The entire stripline can be coated in a 100 micron thick layer of silicone 710 for biocompatibility, as shown schematically in FIG. 7. (Silicone coated pacing leads can remain for decades in blood vessels of pacemaker patients without ill effect.)

By changing the dimensions of the stripline, its impedance can be made to match the impedance of a transducer; as shown in FIG. 8, impedances from 200 to 20 ohms can be matched by adjusting the dimensions of the various parts of the stripline. While a stripline is shown as the source for driving the DGTs in these figures, any means, such as miniature coax lines, etc. familiar to those skilled-in-the-art can be used as well.

Different piezoelectric materials in these transducers will have different impedances for the same dimension transducers. If, for example, PVDF-TrFE coated thin elements are used for the transducers (coating metal with this material to make small spherical transducers is described in "A System for Ultrasonic Beacon-Guidance of Catheters and Other Minimally Invasive Devices", Vilkomerson D, and Lyons D, IEEE Transactions on Ultrasonics, Ferrolelectrics and Frequency Control, 44, pg 496; 1997) is used, PVDF-TrFE's relative permittivity coefficient k in Eq. 1(a) is ~100 times less than that of KNN-LT-LS; Eq. 1(a) shows that this would increase the impedance by a factor of 100. However, because the frequency constant Fc for PVDF-TrFe is one-quarter that of KNN-LT-LS (because the speed of sound is much less in PVDF-TrFe that in ceramics), the total effect on the impedance is 100/4 or 25 greater impedance than the 50 ohms of the piezoceramic, or 1250 ohms. As the impedance described by Eq. 1 is inversely proportional to the frequency squared, increasing the frequency by a factor of 2 will reduce the impedance by 4, bringing the impedance to 312 ohms, which is still beyond the range of stripline matching.

However, if six transducer elements are driven in parallel and six receivers in parallel, the impedance will be well-matched and satisfactory operation achieved.

Other transducer materials that are biocompatible, such as the polymer PVF2 and the lead-free ceramic Potassium sodium niobate, and other metals used in implantable devices, such as titanium, platinum, or nitinol, can be used, applying the equations and teachings disclosed here.

Figure 11:
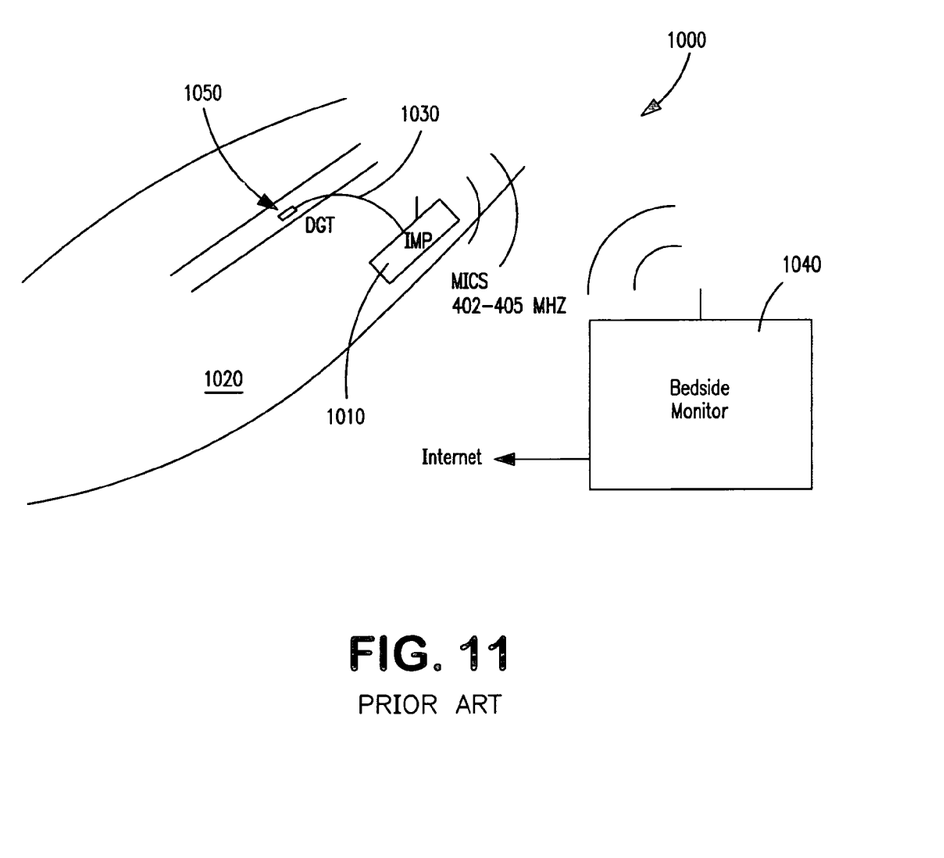
FIG. 11 reproduces an illustration of the system disclosed in FIG. 10 of the '276 application.

The Doppler signals on the stripline can be brought out of the blood vessel, either to outside the body to Doppler electronics through a catheter, similar to the way intravenous lines carry fluids in and out of blood vessels, or brought to small wireless telemetry unit placed outside of the vessel, but underneath the skin, as is done for cardiac pacemakers, where the pacemaker lead enters the subclavian vein on its path to the heart and is connected to pacing electronics in a pouch made under the skin. (By being inside the skin, there is no chance for infective agents to enter the body, as happens with catheters.) As FIG. 11 shows a battery-powered device 1010 to operate the flow-measuring device and transmit the Doppler signals to a bedside monitor 1040. As known to those skilled in the art, in addition to battery power various other means of powering such telemetry devices are known, such as inductively coupling power to them, or harvesting the mechanical energy of pulsing vessels, moving limbs, etc. FIG. 11 is the same FIG. 10 of the copending '276 application.

Figure 9A:
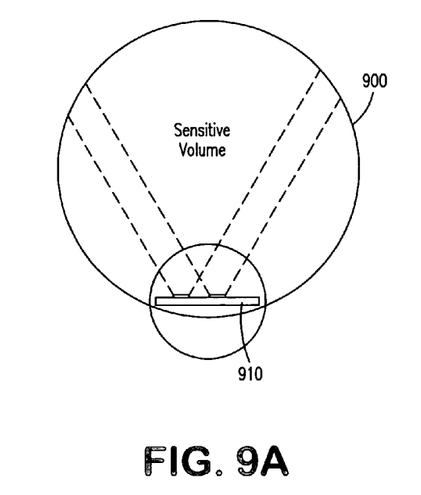
FIG. 9 depicts the use of a stripline-compatible configuration to carry two transducers, one DGT and the other non-DGT along the bottom of a vessel.
Figure 9B:
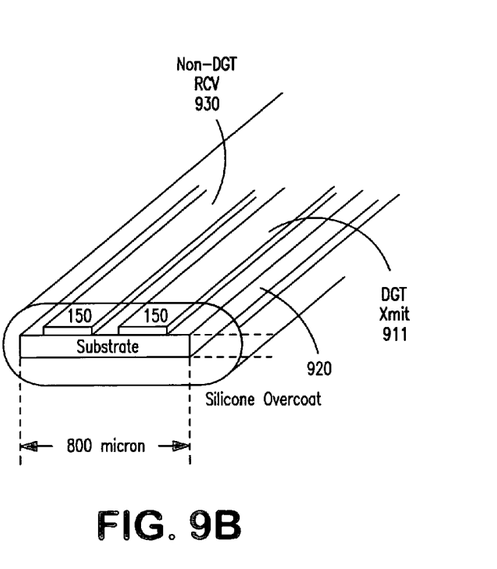
Figure 10:
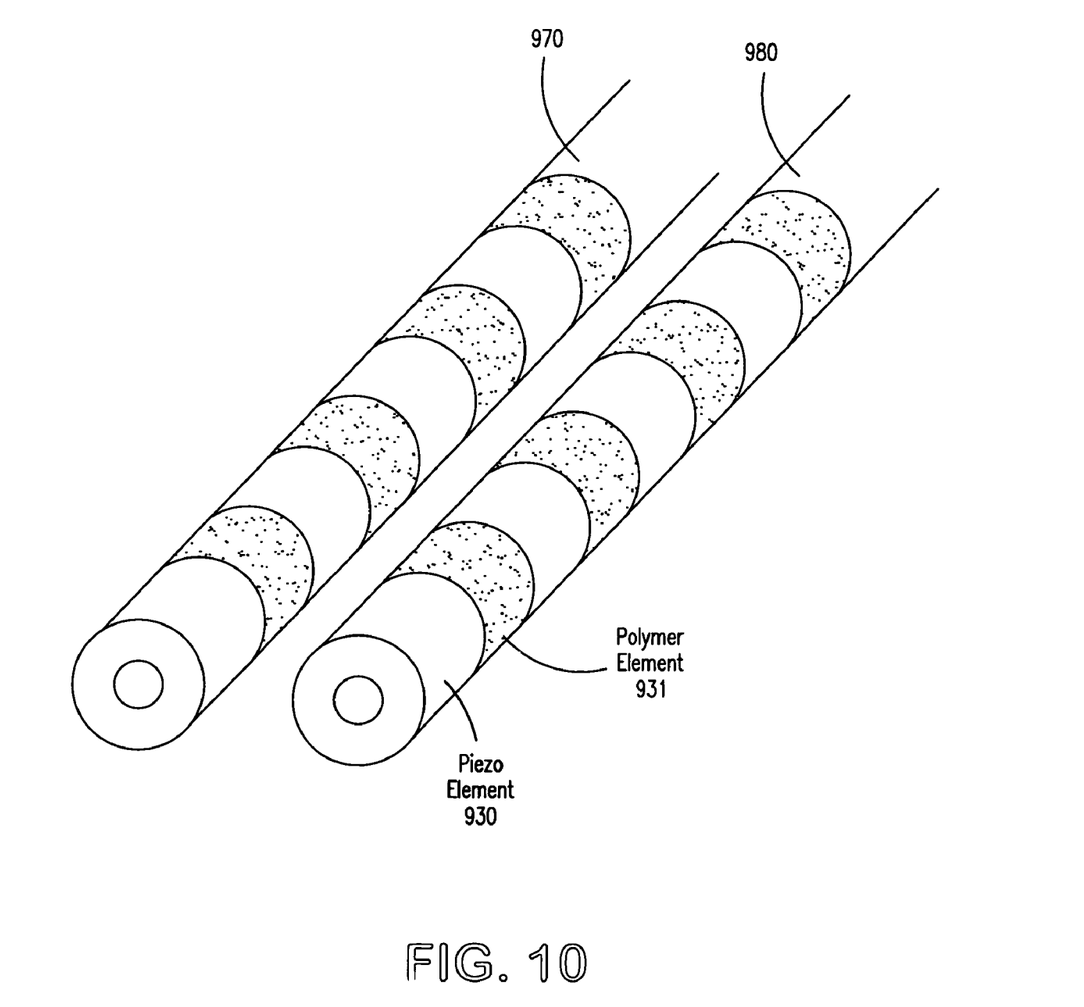
FIG. 10 shows how a tubular version of the transducers shown in FIG. 9 can be constructed.
Figure 14:
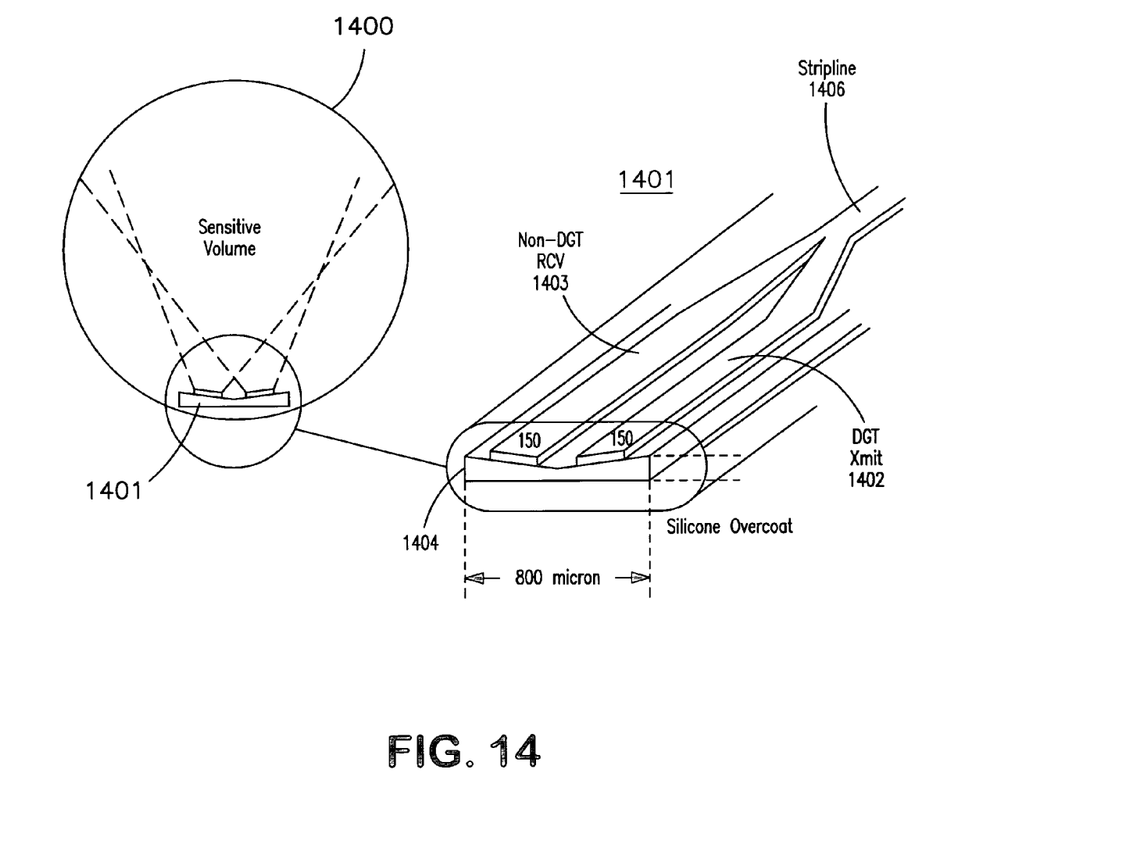
FIG. 14 shows a cross sectional view of a vessel having a canted send-receive structure placed therein.

Further, the stripline structure can be integrated with the DGT and other non-DGT transducers for easy fabrication, as shown in FIG. 14. By placing narrow transducer structures fabricated like those shown in FIG. 2, i.e., that are alternatively reversed poled to form a DGT and uniformly poled to form a non-DGT—but retain the flexibility produced by the polymer intervals, overlapping beams can be formed to produce the sensitive volume needed for Doppler operation. FIG. 9A shows a vessel 900 having a double DGT device 910 placed in the vessel 900 to transmit and receive signals. FIG. 9B shows the transmit DGT 911 positioned on a substrate 920. A non DGT receiver 930 is also on the substrate 920. Other structures can be used in place of the stripline, such as similar to coaxial cables, as shown in FIG. 10, as long as they include the basic DGT structure.

The stripline or other interconnecting (from intravascular device to external connection) structure can be used to carry a single DGT for use in pulse-mode, albeit with the drawbacks of such modes described earlier.

The transducer materials suitable for interconnecting structures include the biocompatible piezoceramics as discussed above, conventional piezoceramics if properly covered to prevent blood or other tissue contact, or various piezopolymers familiar to those skilled in the art. An advantage of the stripline or other connecting-cable configuration for these transducers is that the transducers can be tens of centimeters long, so that the transducer area is greatly increased, which is advantageous for the use of low dielectric transducer materials like PVDF, as it makes the transducer's impedance more easily matched. (The limitation on transducer length is the spatial wavelength of the pulsatile velocity in the blood: the velocity measured will be the average over the length of the transducer; as the spatial wavelength is about 400 centimeters [McDonald's Blood Flow in Arteries, Nichols and O'Rourke, Hodder Arnold, London, 2005, page 64], for accuracy the transducers should be no more than about 1/10 of a velocity wavelength, i.e. 40 centimeters long, which still provides a factor of 20 in length which therefore [see Eq. 1 for the area] therefore reduces impedance by that factor.)

Figure 12:
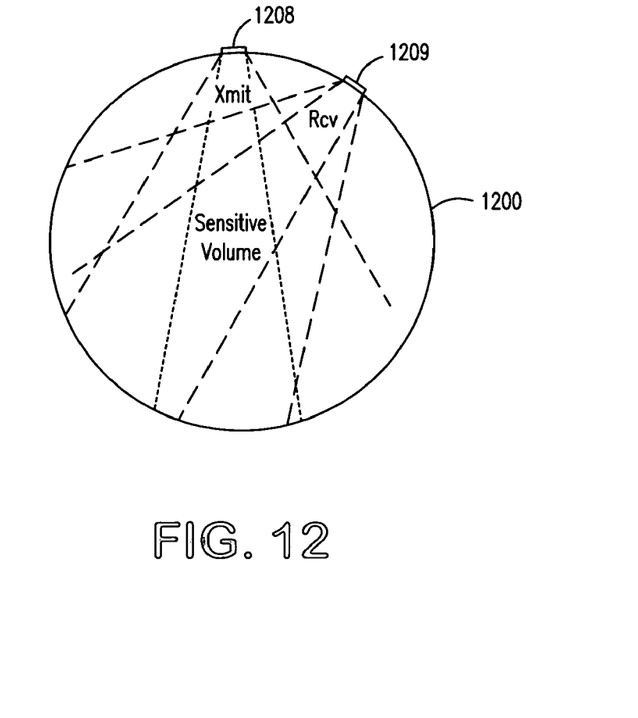
FIG. 12 shows a cross section of a vessel as in FIG. 4 with a receive and a transmit DGT.

Referring to FIG. 12, there is shown a vessel 1200 having a transmit DGT 1208 and receive DGT 1209. As seen both DGTs are placed about the periphery of the vessel 1200 and are separated one from the other. Basically the configuration shown in FIG. 12 is identically the configuration shown in FIG. 4 with a little bit more detail.

Figure 13:
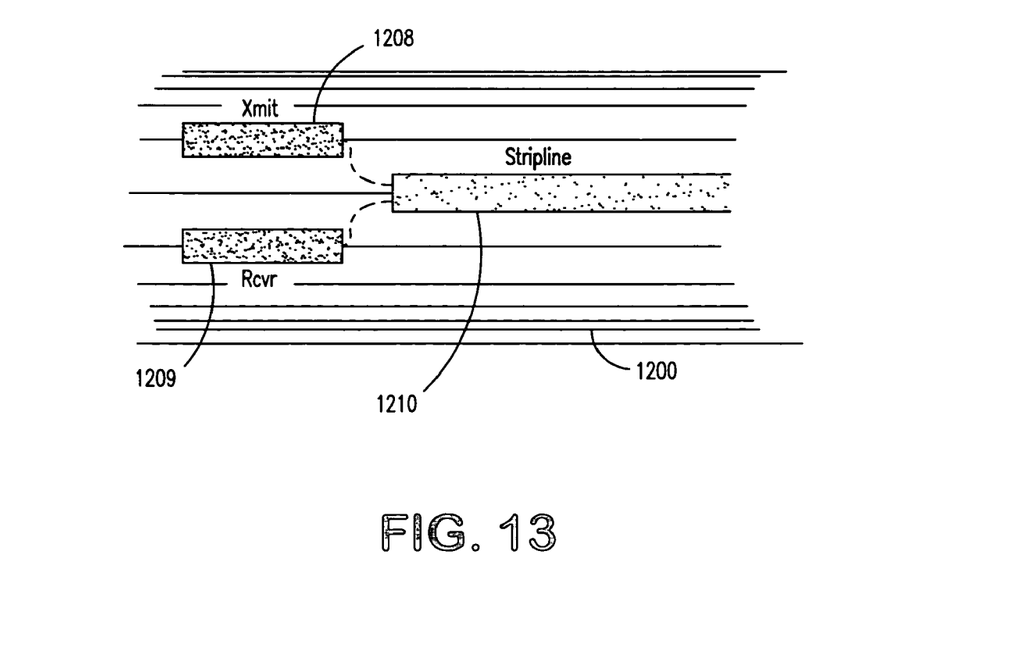
FIG. 13 shows a cross section of a vessel along the length with DGT transmit and receive transducers and a double stripline for connecting to them.

Referring to FIG. 13, there is shown a view of the vessel 1200 along the length showing the positioning of the transmit DGT 1208 and a receive DGT 1209. Both DGTs are energized by a stripline 1210 which is also inserted in the wall of the vessel and which is capable of propagating suitable signals to energize the DGTs in order to enable them to produce the Doppler signal required for measuring of blood flow.

Referring to FIG. 14, there is shown a structure similar to the structure shown in FIG. 9. In any event, in FIG. 14 a vessel 1400 has about the periphery a DGT structure 1401. The structure 1401 includes a first non DGT receiver 1403 and a second DGT transmitter 1402. Both devices terminate in a stripline portion 1406 which essentially provides a signal. As seen the devices are canted or at an angle to enable more efficient transmission as shown in FIG. 14 for example. Thus, as one can ascertain from the above, one is able to produce narrow DOT devices by employing diffraction of the narrow transducer to generate coverage in two dimensions and to generate a third dimension from the diffraction generated by the DGT or grating structure. By using Doppler with two beams simultaneously in a distributed fashion over an'extended transducer length, one can achieve enough area to produce good impedance matching at the high frequencies. The devices meet the need for long extended transducers suitable for deployment in a circulatory system without affecting blood flow. The characteristics of blood flow require that the velocity spatial wavelength is 4 meters or so and therefore one can provide a sensor which is one tenth of the wavelength so that the change in velocity along the length is minimal. This device can still be 40 centimeters long and because of that length one can obtain enough capacitance so that signals can be applied and Doppler signals generated can be responded to. Thus, one uses a combination of diffraction intrinsic to a narrow element to spread the beam in one direction. One can utilize a phase alternating configuration for the DGT as for example that shown in FIG. 2A. The phase alternating DGT forces the beam to go along the length of the element, therefore the polarization alternation causes the beam to spread because the element is narrow and it allows the use therefore of a extremely long element giving large capacitance and providing good Doppler discrimination.

It should be apparent to those skilled in the art that other modifications and configurations are contemplated, all of which are deemed to be incorporated within the spirit and scope of the claims appended hereto.

What is claimed is:

1. An apparatus for measuring blood flow, comprising:
   a first elongated narrow ribbon-like diffraction grating transducer (DGT) having a given length, said DGT comprising alternatively polarized sections of piezoelectric media, each section of piezoelectric media being separated by separation media,
   means for applying a signal to said DGT to cause said DGT to produce a propagating diffracted beam therefrom in one direction relatively parallel to the length of said DGT and due to the narrow extent thereof said beam spreads in a direction perpendicular to said length.

2. The apparatus according to claim 1, wherein said means for applying a signal includes a stripline.

3. The apparatus according to claim 1, further including:
   a second elongated narrow transducer associated with said first transducer, said second transducer being operative to receive Doppler-shifted ultrasound frequencies produced by scattering of ultrasound from said first transducer by flowing blood.

4. The apparatus according to claim 1, wherein said transducer is of a length sufficient to cause said transducer to present a useful capacitance at ultrasonic frequencies.

5. The apparatus according to claim 4, wherein the length is between 5 to 400 millimeters.

6. The apparatus according to claim 1, wherein said separation media is a polymer.

7. An apparatus for measuring flow in a vessel, comprising:
   a diffraction grating transducer (DGT) positioned at the periphery of a vessel and being substantially longer than the width thereof, said DGT having a ribbon-like appearance and having alternately polarized sections to enable said DGT to produce by diffraction a propagating beam in a given direction along a path,
   a second transducer positioned at the periphery of said vessel and spaced apart from said DGT, said second transducer being of a length and width relatively the same as said DGT and having a ribbon-like appearance and having non-polarized sections, and operative to receive Doppler-shifted ultrasound frequencies produced by the flow of blood through said propagating beam from said DGT.

8. The apparatus according to claim 7, wherein said length is between 5 to 400 millimeters with a width of less than 10 wavelengths of the frequency of operation.

9. The apparatus according to claim 7, wherein said propagated signal is at a frequency between 5 MHz to 40 MHz.

10. The apparatus according to claim 7, wherein said DGT has piezoelectric alternately, polarized sections.

11. The apparatus according to claim 10, wherein said polarized sections are separated one from the other by a polymer.

12. The apparatus according to claim 7, including:
    means for providing a signal to said DGT to produce said propagating beam and for providing a signal received from said second transducer to reach a detection means.

13. The apparatus according to claim 12, wherein said means for generating includes a stripline.

14. The apparatus according to claim 7, wherein said DGT and said second transducer are mounted on a common substrate and are relatively parallel to one another.

15. The apparatus according to claim 14, wherein said DGT and second transducer are canted with regard to one another.

16. The apparatus according to claim 7, wherein said DGT and said second transducer are bio-compatible.

17. The apparatus according to claim 7, wherein said DGT and said second transducer are flexible.

* * * * *